United States Patent [19]

Welter et al.

[11] 4,397,858

[45] Aug. 9, 1983

[54] TREATMENT OF RHEUMATISM AND ARTERIOSCLEROSIS WITH N-HALOGENOPHENYL-BENZISO-THIAZOLES

[75] Inventors: André Welter; Hans-Heiner Lautenschläger; Eugen Etschenberg, all of Cologne; Sigurd Leyck, Pulheim, all of Fed. Rep. of Germany

[73] Assignee: A. Nattermann & Cie GmbH, Cologne, Fed. Rep. of Germany

[21] Appl. No.: 313,810

[22] Filed: Oct. 22, 1981

[30] Foreign Application Priority Data

Oct. 31, 1980 [DE] Fed. Rep. of Germany ....... 3041036

[51] Int. Cl.³ .......................................... A61K 31/425
[52] U.S. Cl. .................................... 424/270; 548/209
[58] Field of Search .......................................... 424/270

[56] References Cited

U.S. PATENT DOCUMENTS 3,012,039 12/1961 Morley ................................ 548/209
3,862,955 1/1975 Grivas ............................ 546/255 X

OTHER PUBLICATIONS

*Chemical Abstracts*, 89:108923e (1978).
Fischer, R., et al., *Arzneim.-Forsch.*, 1964, 14, 1301-1306.
Rufer, C., et al., *Eur. J. Med. Chem.-Chim. Ther.* 1978, 13(2), 193-198.

*Primary Examiner*—Richard A. Schwartz
*Attorney, Agent, or Firm*—Pearne, Gordon, Sessions, McCoy, Granger & Tilberry

[57] ABSTRACT

The invention relates to the new use of certain benzisothiazoles corresponding to the following general formula:

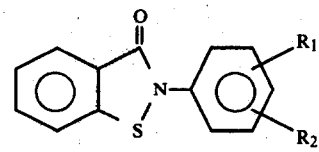

wherein $R_1$ represents chlorine, fluorine or bromine, and $R_2$ represents hydrogen, chlorine, fluorine or bromine, in the treatment of phlogistic and/or arteriosclerotic processes.

3 Claims, No Drawings

TREATMENT OF RHEUMATISM AND ARTERIOSCLEROSIS WITH N-HALOGENOPHENYL-BENZISOTHIAZOLES

BACKGROUND OF THE INVENTION

This invention relates to the use of certain benzisothiazoles in the treatment and prophylaxis of phlogistic and/or arteriosclerotic processes and in the control of the illnesses which they cause, particularly in human beings or even in animals.

SUMMARY OF THE INVENTION

The benzisothiazoles used in accordance with the invention correspond to the following general formula:

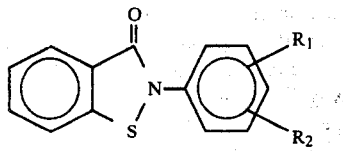

in which $R_1$ represents chlorine, fluorine or bromine and $R_2$ represents hydrogen, chlorine, fluorine or bromine. The following are examples of compounds such as these:

2-(4-fluorophenyl)-1,2-benzisothiazol-3(2H)-one
2-(2-chlorophenyl)-1,2-benzisothiazol-3(2H)-one
2-(3-chlorophenyl)-1,2-benzisothiazol-3(2H)-one
2-(2,3-dichlorophenyl)-1,2-benzisothiazol-3(2H)-one
2-(2,6-dichlorophenyl)-1,2-benzisothiazol-3(2H)-one
2-(3,4-dichlorophenyl)-1,2-benzisothiazol-3(2H)-one
2-(2,4-dichlorophenyl)-1,2-benzisothiazol-3(2H)-one
2-(2,5-dichlorophenyl)-1,2-benzisothiazol-3(2H)-one
2-(4-bromophenyl)-1,2-benzisothiazol-3(2H)-one, but more particularly
2-(4-chlorophenyl)-1,2-benzisothiazol-3(2H)-one.

DETAILED DESCRIPTION OF THE INVENTION

The benzisothiazoles corresponding to general formula I are for the most part known compounds (German Pat. No. 2,119,730) or may be obtained by the process described therein using corresponding starting materials.

Some of the known compounds show bactericidal and fungicidal activity (Arzneimittel-Forsch. 1964, 14, 1301-06). Other forms of therapeutic activity have never been reported.

It has now surprisingly been found that the benzisothiazoles corresponding to general formula I show pronounced antiphlogistic and anti-arteriosclerotic activity and are distinguished from the therapeutically used inflammation-inhibiting compounds by their low toxicity and by their extremely high compatibility with the stomach as reflected in the absence of ulcers.

The outstanding antiphlogistic properties and high compatibility of the benzisothiazoles used in accordance with the invention were determined, for example, by the following tests. Indometacin (1-(p-chlorobenzoyl)-5-methoxy-2-methyl-3-indole acetic acid) was used for comparison.

1. Rat paw oedema test

Determination of antiphlogistic activity by HILLEBRECHT's rat paw oedema test (J. HILLEBRECHT, Arzeim. Forsch. 1954, Vol. 4, page 607). An oedema was produced in one of the rear paws of rats weighing from 120 g to 150 g by the subplantar injection of carragenin (0.5% in a 0.9% NaCl-solution) in a quantity of 0.1 ml of solution per paw. After administration of the test substance, which generally should not exceed a volume of 10 ml per kg of body weight, the volume of the paw is determined in an overflow. After 3 hours, the final value is determined. For each dose, the test is carried out with 10 test animals and 10 control animals of one sex and repeated with the same number of animals of the other sex. For the purposes of evaluation, inhibition of the oedema is expressed as a percentage on relation to the control group. The following values were obtained:

TABLE 1:

| | Oedema inhibition in rats | | | | | |
|---|---|---|---|---|---|---|
| | 2-(4-chlorophenyl)-1,2-benzisothiazol-3(2H)-one | | | Indometacin | | |
| Dose (mg/kg p.o.) | 0.01 | 0.1 | 1.0 | 3.8 | 5.6 | |
| Inhibition (%) | −13 | −22 | −36 | −26 | −45 | |
| Dose (mg/kg i.m.) | 0.1 | 1.0 | 10 | 1.0 | 3.2 | 10 |
| Inhibition (%) | −36 | −26 | −33 | −9 | −23 | −33 |

Granuloma test (Cotton pellet test) according to R. MEIER et al. Experientia 6, 469 (1950)

In this test, cottonwool pellets impregnated with croton oil were implanted subcutaneously in the test animals (rats) to induce the formation of granulomas in the connective tissue. After the animals had been killed, the granulomas were excised and weighed moist or dry. The anti-proliferative effect of an antiphlogistic is reflected in light weights of the granulomas by comparison with untreated controls.

TABLE 2:

| | Anti-proliferative effect | | | | | |
|---|---|---|---|---|---|---|
| | 2-(4-chlorophenyl)-1,2-benzisothiazol-3(2H)-one | | | Indometacin | | |
| Dose (mg/kg p.o.) | 0.1 | 1.0 | 10 | 1 | 3.2 | 5.6 |
| Reduction in weight of the granulomas (%) | −26 | −43 | −44 | −21 | −7 | −6 |

3. Adjuvant arthritis (C. M. PEARSON, proc.Soc.exp.Biol. 91, 95–101 (1956)

10 Wistar rats weighing from 120 g to 150 g are used per dose. The same number of animals is used for control purposes. An arthritis is induced by the administration of 0.5 ml of Freund's adjuvant by subplantar injection. The test lasts 17 days. At the beginning of the test, the paw volume of all four extremities is determined and used as the starting value. Further volume measurements are carried out on the 8th, 14th and 17th days of the test. For evaluation purposes, the difference between the starting volume and final volume of the paws both of the test group and of the control group is calculated and inhibition expressed as a percentage.

TABLE 3:

| | Adjuvant arthritis in rats (p.o.) | | | |
|---|---|---|---|---|
| | 2-(4-chlorophenyl)-1,2-benzisothiazol-3(2H)-one | | Indometacin | |
| Dose (mg/kg p.o.) | 1 | 3.2 | 0.32 | 1.0 |

TABLE 3:-continued

| | Adjuvant arthritis in rats (p.o.) | | | |
|---|---|---|---|---|
| | 2-(4-chlorophenyl)-1,2-benzisothiazol-3(2H)-one | | Indometacin | |
| Inhibition (%) | | | | |
| 7th day p.i. | −27 | −46 | −20 | −50 |
| 14th day p.i. | −44 | −51 | −26 | −40 |
| 17th day p.i. | −45 | −56 | −33 | −40 |

4. Ulcer test

Ulcer formation was determined in accordance with W. J. R. WHITTLE, Brit.J.Pharmacology 1975, Vol. 55, pages 242 to 243; L. MARIANI, Europ. J. Toxicol. Environ, 1975, Vol. 8, pages 335–339; R. MENGUY and L. DESBAILLETS, Proc.Soc.Exp.Bio. Vol. 125, page 1108. In the tests, 10 female and 10 male Wistar rats (120 g–150 g which had been fed on a pure carbohydrate diet for 2 days and subsequently kept without food for 16 hours) were used per dose and control. A bleeding stomach ulcer is induced by oral administration of the active principle. After 3.5 hours, the animals are killed, their stomachs removed, cut open along the major curvature and stretched across a Styropor plate. The frequency and extent of average ulcer formation in the test and control groups is determined. Under these conditions, all hitherto known, therapeutically useable, non-steroidal antiphlogistics induce ulcerations of the stomach mucosa in the therapeutic dosage.

TABLE 4:

| | Ulcer-inducing effect in rats | | | | | |
|---|---|---|---|---|---|---|
| | 2-(4-chlorophenyl)-1,2-benzisothiazol-3(2H)-one | | | Indometacin | | |
| Dose (mg/kg p.o.) | 1 | 10 | 100 | 3.2 | 5.6 | 7.5 |
| Effect | 0 | 0 | 0 | ++ | +++ | +++ |

0 = no ulcer induction
+ = moderate ulcer induction
++ = serious ulcer induction
+++ = very serious ulcer induction

TABLE 5:

| | Toxicity | |
|---|---|---|
| | 2-(4-chlorophenyl)-1,2-benzisothiazol-3(2H)-one | Indometacin |
| Mice, oral | | |
| Dose (mg/kg p.o.) | 3   160 | 38 |
| Lethality (%) | 0 | 50 |

As can be seen from the pharmacological tests, the benzisothiazoles corresponding to general formula I above, even when administered in very small doses, show pronounced antiphlogistic activity, extremely low toxicity and, even when administered in fairly large doses, no ulcer formation.

The active principle may be used in any form, for example systemic, in human or veterinary medicine, provided that the build up and maintenance of adequate levels of active principle in the blood or tissue is guaranteed. This result may be achieved by oral, rectal or parenteral administration in suitable doses. The active principle is with advantage pharmaceutically formulated in individual doses adapted to the required form of administration, such as for example tablets, dragrees, capsules, suppositories, granulates, solutions, emulsions, suspensions, sols or gels. For building up and maintaining adequate blood or tissue levels, the daily dose amounts to between 30 and 300 mg and preferably to between 50 and 200 mg and may be administered one or more times a day, preferably 2 to 3 times a day.

For producing pharmaceutical preparations containing benzisothiazoles of general formula I as their active component, the active principle may be used either as such or in combination with suitable pharmaceutical vehicles and formulated in the usual way.

Suitable vehicles for the preparation of oral formulations, for example in the form of tablets, capsules, granules or powders, are calcium carbonate, calcium phosphate, starch, sugar, lactose, talcum, magnesium stearate, gelatin, polyvinyl pyrrolidone, gum arabic, sorbitol, microcrystalline cellulose, polyethylene glycol, carboxy methyl cellulose, shellac and the like. The tablets may be coated in the usual way. Liquid formulations for oral administration may be made up in the form of aqueous or oily suspensions or solutions, in the form of a syrup, an elixir and the like. These are prepared in the usual way. Injectable formulations may be aqueous or oily suspensions or solutions, powder-form compositions containing a filler and freeze-dried preparations which are dissolved before application, and the like. These formulations are prepared in the usual way.

The benzisothiazoles used in accordance with the invention may also be used in the form of suppositories for rectal administration, the suppositories containing pharmaceutically compatible vehicles which are known per se, for example polyethylene glycol, lanolin, cocoa butter, Witepsol ®, etc. External preparations are preferably made up in the form of ointments or creams which are prepared in the usual way using standard ingredients.

EXAMPLE 1

Tablets 2-(4-chlorophenyl)-1,2-benzisothiazol-3(2H)-one—30 mg
Lactose—150 mg
Crystalline cellulose—50 mg
Calcium carboxymethyl cellulose—7 mg
Magnesium stearate—3 mg The substances listed above are mixed and pressed in the usual way. The pressings obtained may optionally be coated with a standard film.

EXAMPLE 2

Capsules 2-(4-chlorophenyl)-1,2-benzisothiazol-3(2H)-one—30 mg
Lactose—102 mg
Crystalline cellulose—56 mg
Colloidal silicon dioxide—2 mg The substances listed above are mixed, granulated and introduced into hard gelatin capsules by standard methods.

EXAMPLE 3

Tablets 2-(4-chlorophenyl)-1,2-benzisothiazol-3(2H)-one—50 mg
Microcrystalline cellulose—150 mg
Cutina HR—15 mg
Hydroxypropyl methyl cellulose phthalate—20 mg

EXAMPLE 4

Capsules 2-(4-chlorophenyl)-1,2-benzisothiazol-3(2H)-one—50 mg

Talcum—5 mg

Aerosil 200—10 mg are mixed, granulated and introduced into hard gelatin capsules.

What we claim is:

1. A method for the treatment and prophylaxis of arthritis, inflammation and/or arteriosclerosis and resulting illnesses in humans or animals, which comprises administering to an animal an effective amount of a benzisothiazole corresponding to the following general formula:

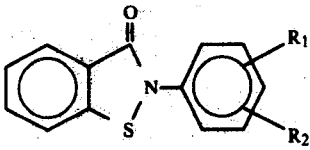

wherein $R_1$ represents a radical selected from the group consisting of chlorine, fluorine and bromine, and $R_2$ represents a radical selected from the group consisting of hydrogen, chlorine, fluorine and bromine.

2. A method according to claim 1, wherein the animal is a human being.

3. A method according to claim 1, wherein the benzisothiazole is 2-(4-chlorophenyl)-1,2-benzisothiazol-3(2H)-one.